United States Patent
Duhm et al.

(10) Patent No.: US 6,783,487 B2
(45) Date of Patent: Aug. 31, 2004

(54) PANT-TYPE PERSONAL CARE ARTICLES, AND METHODS OF MAKING AND USING SUCH PERSONAL CARE ARTICLES

(75) Inventors: Daniel Mark Duhm, Greenville, WI (US); Keith Joseph Renard, Oshkosh, WI (US); Denise Marie Bell Murie, Neenah, WI (US); Russell Evan Thorson, Appleton, WI (US); Suzanne Marie Schmoker, Oshkosh, WI (US); Sarah Jane Marie Freiburger, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 55 days.

(21) Appl. No.: 09/834,869

(22) Filed: Apr. 13, 2001

(65) Prior Publication Data

US 2002/0151422 A1 Oct. 17, 2002

(51) Int. Cl.[7] .................................................. B31B 1/64

(52) U.S. Cl. ...................... 493/194; 493/475; 493/210; 156/66

(58) Field of Search .......................... 156/66, 204, 217; 604/385.2, 390, 391, 394; 493/194, 199, 210, 373, 475

(56) References Cited

U.S. PATENT DOCUMENTS

| | | | |
|---|---|---|---|
| 2,834,347 A | 5/1958 | Connally | 128/284 |
| 3,800,796 A | 4/1974 | Jacob | 128/284 |
| 4,699,622 A | 10/1987 | Toussant et al. | 604/389 |
| 4,743,239 A | 5/1988 | Cole | 604/385 |

(List continued on next page.)

FOREIGN PATENT DOCUMENTS

| | | | |
|---|---|---|---|
| CA | 2096672 | 11/1997 | A61F/13/56 |
| DE | 197 32 499 | 2/1999 | A61F/13/15 |
| EP | 0 570 980 | 5/1993 | A61F/13/15 |
| EP | 0 832 628 | 4/1998 | A61F/13/15 |
| EP | 1044285 A1 | 5/2000 | A61F/13/15 |
| EP | 1013251 A1 | 6/2000 | A61F/13/15 |
| JP | 03176053 | 7/1991 | A61F/13/15 |
| WO | WO 97/23180 | 7/1997 | A61F/13/15 |
| WO | WO 99/65438 | 12/1999 | A61F/13/15 |
| WO | WO 00/20208 | 4/2000 | B32B/27/02 |
| WO | WO 01/13844 | 3/2001 | A61F/13/15 |

OTHER PUBLICATIONS

Heller, et al., U.S. Pat. Publication No. 2002/0148557, published Oct. 17, 2002, entitled *Method of Assembling Personal Care Absorbent Article*.

(List continued on next page.)

*Primary Examiner*—Eugene Kim
(74) *Attorney, Agent, or Firm*—Dority & Manning, P.A.

(57) ABSTRACT

The invention comprises methods and apparatus of changing from manufacture of pant-type refastenable articles of a first size to manufacture of articles of a second different size in a process for manufacturing pant-type refastenable personal care articles. A respective such personal care article has a front portion, rear portion, and crotch portion. The personal care article also has a fastener-receptive area at the front portion for receiving fasteners thereon, first and second fasteners on opposing sides of the fastener-receptive area, and first and second lines of weakness on opposing sides of the fastener-receptive area and between the fastener-receptive area and the respective first and second fasteners. The method comprises changing spacing between the fastener-receptive area and at least one of the first and second fasteners while maintaining the first and second lines of weakness between the fastener-receptive area and the respective first and second fasteners.

20 Claims, 4 Drawing Sheets

U.S. PATENT DOCUMENTS

| | | | |
|---|---|---|---|
| 4,773,906 A * | 9/1988 | Krushel | 604/391 |
| 4,801,298 A * | 1/1989 | Sorenson et al. | 604/384 |
| 5,261,901 A * | 11/1993 | Guay | 604/391 |
| 5,370,634 A | 12/1994 | Ando et al. | 604/385.1 |
| 5,624,428 A | 4/1997 | Sauer | 604/391 |
| 5,690,627 A | 11/1997 | Clear et al. | 604/385.2 |
| 5,788,797 A | 8/1998 | Herrin et al. | 156/73.1 |
| 5,818,719 A * | 10/1998 | Brandon et al. | 700/125 |
| 5,830,206 A | 11/1998 | Larsson | 604/390 |
| 5,846,232 A | 12/1998 | Serbiak et al. | |
| 5,858,515 A | 1/1999 | Stokes et al. | 428/195 |
| 5,930,139 A | 7/1999 | Chapdelaine et al. | 364/468.25 |
| 6,022,430 A | 2/2000 | Blenke et al. | 156/73.1 |
| 6,022,432 A | 2/2000 | Elsberg et al. | 156/73.1 |
| 6,027,484 A | 2/2000 | Romare | 604/386 |
| 6,036,805 A | 3/2000 | McNichols | 156/227 |
| 6,077,379 A | 6/2000 | Herrin et al. | 156/269 |
| 6,113,717 A | 9/2000 | Vogt et al. | 156/73.1 |
| 6,210,388 B1 * | 4/2001 | Widlund et al. | 604/390 |
| 6,277,223 B1 | 8/2001 | Herrin et al. | 156/73.1 |
| 6,328,725 B2 | 12/2001 | Fernfors | 604/391 |
| 6,375,646 B1 | 4/2002 | Widlund et al. | 604/385.3 |
| 6,383,431 B1 * | 5/2002 | Dobrin et al. | 264/154 |
| 6,454,888 B1 | 9/2002 | Murie et al. | |
| 6,461,344 B1 * | 10/2002 | Widlund et al. | 604/390 |

OTHER PUBLICATIONS

Sorenson, et al., U.S. Pat. Publication No. 2002/0157778, published Oct. 31, 2002, entitled *Multiple Component Web*.

Fell et al., U.S. Pat Publication No. 2002/0169432, published Nov. 14, 2002, entitled *Absorbent Garment With Expandable Absorbent Element*.

Gompel et al., U.S. Pat. Publication No. 2003/0004487, published Jan. 2, 2003, entitled *Expandable Absorbent Garment*.

Price et al., U.S. Pat. Publication No. 2003/0028166, published Feb. 6, 2003, entitled *Absorbent Garment Having a Body Conforming Absorbent Composite*.

Sanders et al., U.S. Pat. Publication No. 2003/0055389, published Mar. 20, 2003, entitled *Method and Apparatus for Assembling Refastenable Absorbent Germent*.

Vogt, et al., U.S. Pat. Publication No. 2003/0088223, published May 8, 2003, entitled *Passive Bonds for Personal Care Article*.

Price et al., U.S. Pat. Publication No. 2003/0124303, published Jul. 3, 2003, entitled *Refastenable Absorbent Garment*.

Van Gompel et al., U.S. Pat. Publication No. 2003/0135184, published Jul. 17, 2003, entitled *Refastenable Absorbent Garment and Method For Assembly Thereof*.

Guralski, et al., U.S. Pat. Publication No. 2003/0135192, published Jul. 17, 2003, entitled *Method and Apparatus for Assembling Refastenable Absorbent Garments*.

Mlinar et al., U.S. Pat. Publication No. 2003/0132549, published Jul. 17, 2003, entitled *Method and Apparatus for Weakening a Portion of a Web*.

Price et al., U.S. Pat. Publication No. 2003/0135191, published Jul. 17, 2003, entitled *Refastenable Absorbent Garment*.

Gompel, et al., U.S. application No. 09/854904, filed May 14, 2001, entitled *Absorbent Garment with an Extensible Backsheet*.

Mlinar, et al., U.S. application No. 09/954480, filed Sep. 14, 2001, entitled *Method and Apparatus for Assembling Refastenable Absorbent Garments*.

Sanders, U.S. application No. 09/054478, filed Sep. 14, 2001, entitled *Method and Apparatus for Assembling Refastenable Absorbent Garments*.

\* cited by examiner

PANT-TYPE PERSONAL CARE ARTICLES, AND METHODS OF MAKING AND USING SUCH PERSONAL CARE ARTICLES

BACKGROUND OF THE INVENTION

This invention relates to methods and apparatus for changing sizes in pull-on absorbent personal care articles. More specifically, this invention relates to methods and apparatus for changing sizes in especially the circumferential waist in pull-on refastenable absorbent personal care articles. The methods and apparatus of the invention nullify the counterproductive aspects of down time on manufacturing lines to change and adjust function rolls and other components necessary for changing production from a first article size to a second different article size, of pull-on refastenable absorbent personal care articles.

In conventional methods for fabricating disposable pull-on refastenable absorbent personal care articles of differing sizes, it is known to stop manufacturing line production of personal care articles of a first size to replace and/or reposition function rolls and adjust timing of manufacturing line components to produce personal care articles of a second different size on the same manufacturing line. The down time associated with a conventional such production changeover is typically significant. The main reason for such significant down time is related to conventional methods of changing the product length to effect change in product (e.g. waist) size.

Function rolls are typically either exchanged or moved to compensate for a variety of lengths of any of front portions, back portions, and crotch portions of such absorbent articles, defining differing waist, and optionally crotch, sizes between the first and second sizes of absorbent personal care articles. Similarly, other manufacturing components are typically adapted, for example, knife repeat distances may be adjusted, or a knife or knives may be moved, to compensate for changed cutting requirements. Timing of front fastener panel applicators and hook tab fastener applicators may also need to be adjusted in a machine direction to compensate for waist size differentiation between different sizes of absorbent articles. In sum, the conventional method of making a size change is to shut down the production line and physically adjust or move selected machines in order to effect the change to making a second different size of personal care absorbent article.

A need exists for methods and apparatus for production of pull-on refastenable absorbent personal care articles wherein the methods and apparatus reduce the number of manufacturing elements which must be moved or adjusted, and thereby attenuate down time on a manufacturing line as well as reduce cost to manufacturers by enabling manufacturers to use common manufacturing line components to producing pull-on refastenable absorbent personal care articles having a variety of sizes.

Thus it is an object of this invention to provide methods and apparatus for production of pull-on absorbent personal care articles while attenuating down time on a manufacturing line, as well as to reduce cost to manufacturers by allowing manufacturers to use the same manufacturing line components in producing at least two sizes of pull-on refastenable absorbent personal care articles.

It is another object to provide methods and apparatus for changing product size without changing machine direction product repeat length.

It is a further object to provide methods and apparatus for changing spacing between a landing zone loop structure and cooperating fasteners of personal care articles.

It is still a further object to provide methods and apparatus for changing location of the fastener portion on the front portion of personal care articles.

SUMMARY OF THE DISCLOSURE

In a first family of embodiments, the invention comprehends a method of changing from manufacture of pant-type refastenable personal care articles of a first size to manufacture of such pant-type refastenable personal care articles of a second different size. The method takes place in a process for manufacturing pant-type refastenable personal care articles in a format which includes defining a stream of workpieces connected to each other along a web having an indefinite length. A respective such personal care article has a front portion, a rear portion, and a crotch portion. The method comprises, with respect to each work piece, defining in the web or workpiece a length of material defined in a machine direction wherein activity of such length of material, in combination with other elements of the web or workpiece, determines the size of the pant-like personal care article being so produced, whereby the length of material can be activated to thereby produce relatively larger such personal care articles, or inactivated to produce relatively smaller personal care articles. The method also comprises changing activity of the lengths of material so defined, thereby to affect size change in the respective personal care articles being produced while maintaining the so-defined lengths of material in the web at least until the respective work pieces are separated from the web.

In preferred embodiments, the method includes such workpieces, including the defined length of material, having a common dimension leading edge to leading edge, in the machine direction of such manufacturing process both with inclusion of the length of material and with exclusion of the length of material.

In a second family of embodiments, the invention comprises a method of changing from manufacture of pant-type refastenable articles of a first size to manufacture of such pant-type refastenable articles of a second different size in a process for manufacturing pant-type refastenable personal care articles. A respective such personal care article has a front portion, a rear portion, and a crotch portion. The personal care article also has a fastener-receptive area at the front portion for receiving fasteners thereon, first and second fasteners on opposing sides of the fastener-receptive area, and first and second lines of weakness on opposing sides of the fastener-receptive area and between the fastener-receptive area and the respective first and second fasteners. The first and second lines of weakness can be employed for tearing first and second lateral sections from a central section of the front portion, whereby the first and second fasteners are disposed on the respective first and second lateral sections. The method of changing from manufacture of such pant-type refastenable articles of a first size to manufacture of such pant-type refastenable articles of a second different size, in the manufacturing process, comprises changing spacing between the fastener-receptive area and at least one of the first and second fasteners while maintaining the first and second lines of weakness between the fastener-receptive area and the respective first and second fasteners.

In preferred embodiments, the method includes changing spacing between the fastener-receptive area and both of the first and second fasteners while maintaining the first and second lines of weakness between the fastener-receptive area and the first and second fasteners.

In some embodiments, the method includes changing location of one or both of the respective fasteners on the front portion.

In some embodiments, the method includes changing location of one or both of the respective lines of weakness to maintain spacing between the line or lines of weakness and the respective fastener or fasteners.

In some embodiments, the fastener-receptive area has first and second side edges facing the respective first and second fasteners, and the method includes changing location of at least one of the side edges of the fastener-receptive area, and can include changing location of the respective line of weakness to maintain spacing between the line of weakness and the respective side edge.

In preferred embodiments, the method includes changing locations of both the first and second side edges of the landing zone, and can include changing locations of the lines of weakness to maintain spacing between the respective lines of weakness and the respective side edges.

In a third family of embodiments, the invention comprehends a method of changing from manufacture of pant-type refastenable articles of a first size to manufacture of such pant-type refastenable articles of a second different size, wherein the method comprises changing location of at least one of the first and second fasteners toward or away from the central longitudinal axis while maintaining the respective first or second line of weakness between the respective fastener and the central longitudinal axis. In a process for manufacturing such pant-type refastenable personal care articles, a respective such personal care article has first and second lines of weakness defining first and second side edges of the landing zone, whereby the first and second fasteners are disposed on the respective first and second lateral sections, and the central section of the front portion between the lines of weakness defines the landing zone.

In a fourth family of embodiments, the invention comprehends a method employed in a process for manufacturing pant-type refastenable personal care articles, the process including utilizing first feed apparatus and corresponding first feed settings to feed fasteners to work pieces, and optionally utilizing second feed apparatus and corresponding second feed settings to feed fastener-receptive areas to the work pieces. The method includes at least one of (i) changing the feed settings of the feed apparatus feeding the fasteners to thereby move the locations on the work pieces, of placement of the fasteners, and (ii) relocating the apparatus feeding the fasteners to the work pieces, to thereby move the locations on the work pieces, of placement of the fasteners.

In some embodiments, the process includes cutter apparatus fabricating the lines of weakness in the front portion, the method further comprising relocating the cutter apparatus to thereby move the locations on the work pieces, of fabricating the lines of weakness, or changing the timing of cutting of the lines of weakness to thereby move the locations on the work pieces, of fabricating the lines of weakness.

In some embodiments, the method includes changing the timing of the feed apparatus feeding the fasteners to the work pieces, thereby to move the locations on the work pieces, of placement of the fasteners, while running a manufacturing line and so producing such pant-type refastenable personal care articles.

In a fifth family of embodiments, the invention comprehends a method of manufacturing personal care articles comprising manufacturing an indefinite number of personal care articles of a first size, and reducing size of the personal care articles being manufactured by changing, in each respective personal care article, spacing between respective elements in the front portion of the personal care article and thereby creating excess material in an element represented in the front portion.

In some embodiments, the method includes retaining the excess material in the personal care articles through completion of manufacture, and packaging.

Yet in other embodiments, the method includes removing the excess material in the personal care articles at some point during manufacture, and packaging.

In a sixth family of embodiments, the invention comprehends a pant-type refastenable personal care article having a front portion and a rear portion, and a crotch portion between the front portion and the rear portion. Each of the front and rear portions comprises first and second side edges. The pant-type refastenable personal care article comprises an outer liquid-impermeable cover, an inner liquid-permeable liner, and an absorbent core disposed between the outer cover and inner liner. The pant-type refastenable personal care article has a first length represented by a first distance across a front portion of the pant-type refastenable personal care article, and a second length represented by a second distance across a rear portion of the pant-type refastenable personal care article. The pant-type refastenable personal care article comprises a landing zone disposed at a portion of the front portion of the outer cover, first and second fasteners, each disposed laterally of the landing zone, and first, second, third, and fourth lines of weakness. The first line of weakness and the third line of weakness are disposed between the landing zone and the first fastener. The second line of weakness and the fourth line of weakness are disposed between the landing zone and the second fastener. The portion of the pant-type refastenable personal care article disposed between the first and third lines of weakness defines a first length of material, and the portion of the pant-type refastenable personal care article disposed between the second and fourth lines of weakness defines a second length of material.

In preferred embodiments, the invention further comprises a third fastener disposed on the first length of material, and a fourth fastener disposed on the second length of material.

In some embodiments, the first length of material and second length of material remain attached to the personal care article while the personal care article is being worn by a wearer.

In other embodiments, the first length of material and second length of material are removed by a wearer of the personal care article.

Yet in other embodiments, the first length of material and second length of material are removed by a manufacturer of the personal care article.

The invention is not limited in its application to the details of the construction and the arrangement of the components set forth in the following description or illustrated in the drawings. The invention is capable of other embodiments or of being practiced or carried out in various other ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

The invention relates to refastenable pant-type personal care articles, to methods of making such articles by changing effective waist sizing, and to methods of using such personal care articles. The waist sizing change is accomplished by changing location of placement of fastener material and optionally by changing location of creation of lines of weakness associated with sides of a fastener reception area. The fastener material then must be moved a greater distance from its locus of placement on the personal care article, during use, in order to engage the reception area thereby to reduce the waist circumference of the resultant refastenable pant personal care article.

Figure 1A:
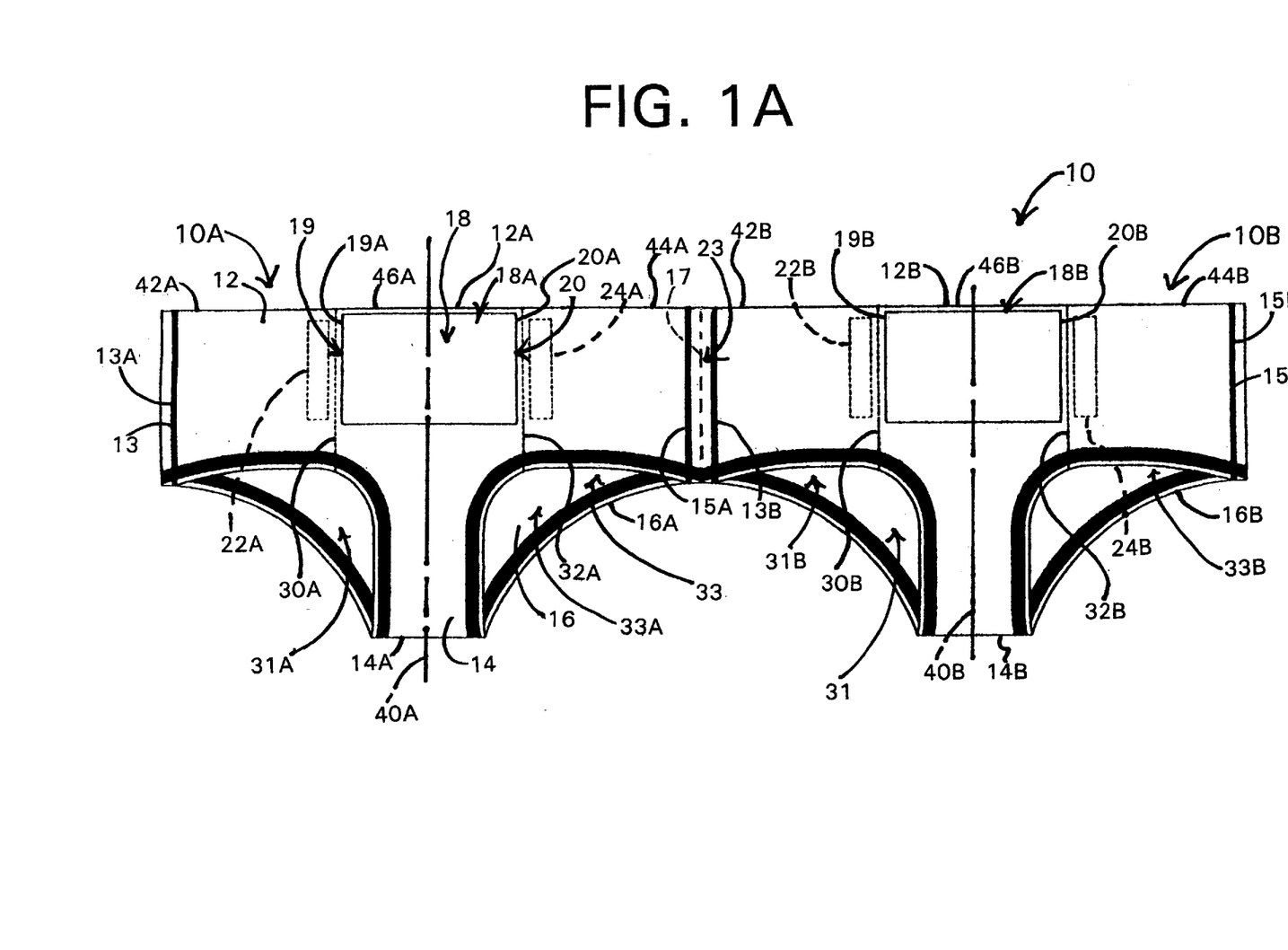
FIG. 1A shows an elevation view of first and second personal care articles which can be made employing methods of the invention and demonstrating a first size.
Figure 1B:
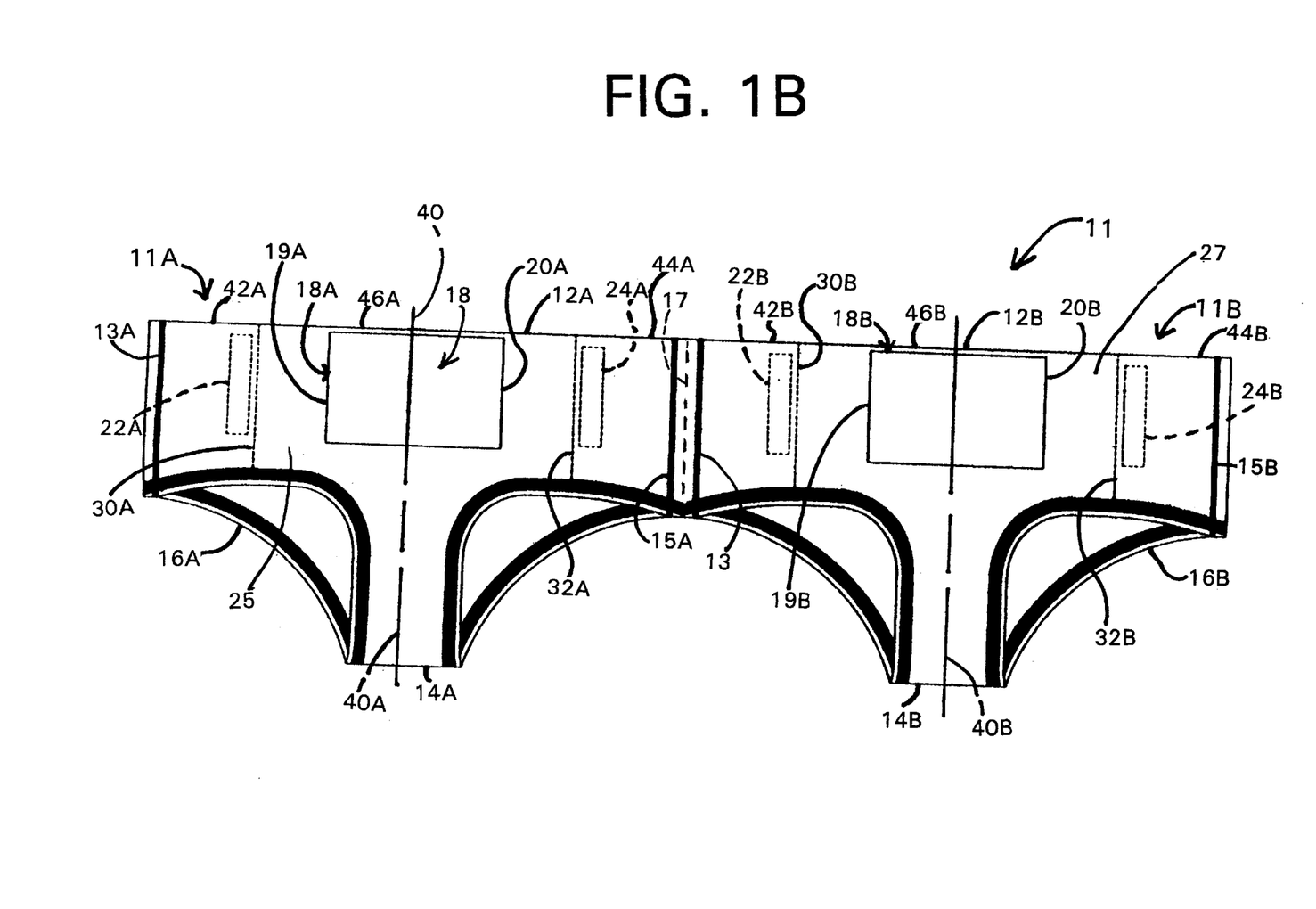
FIG. 1B shows an elevation view of first and second personal care articles which can be made employing methods of the invention and demonstrating a second size in combination with the same repeat length as in the personal care article of FIG. 1A.

FIG. 1A illustrates a first refastenable pant-type personal care article 10A and a second refastenable pant-type personal care article 10B, collectively articles 10, both reflecting potential for a first refastened size. Similarly, FIG. 1B shows a first refastenable pant-type personal care article 11A and a second refastenable pant-type personal care article 11B, collectively articles 11, both reflecting potential for a second refastened size. Personal care articles 11 of FIG. 1B represent a potentially relatively smaller size personal care article than personal care articles 10 of FIG. 1A.

Figure 3:
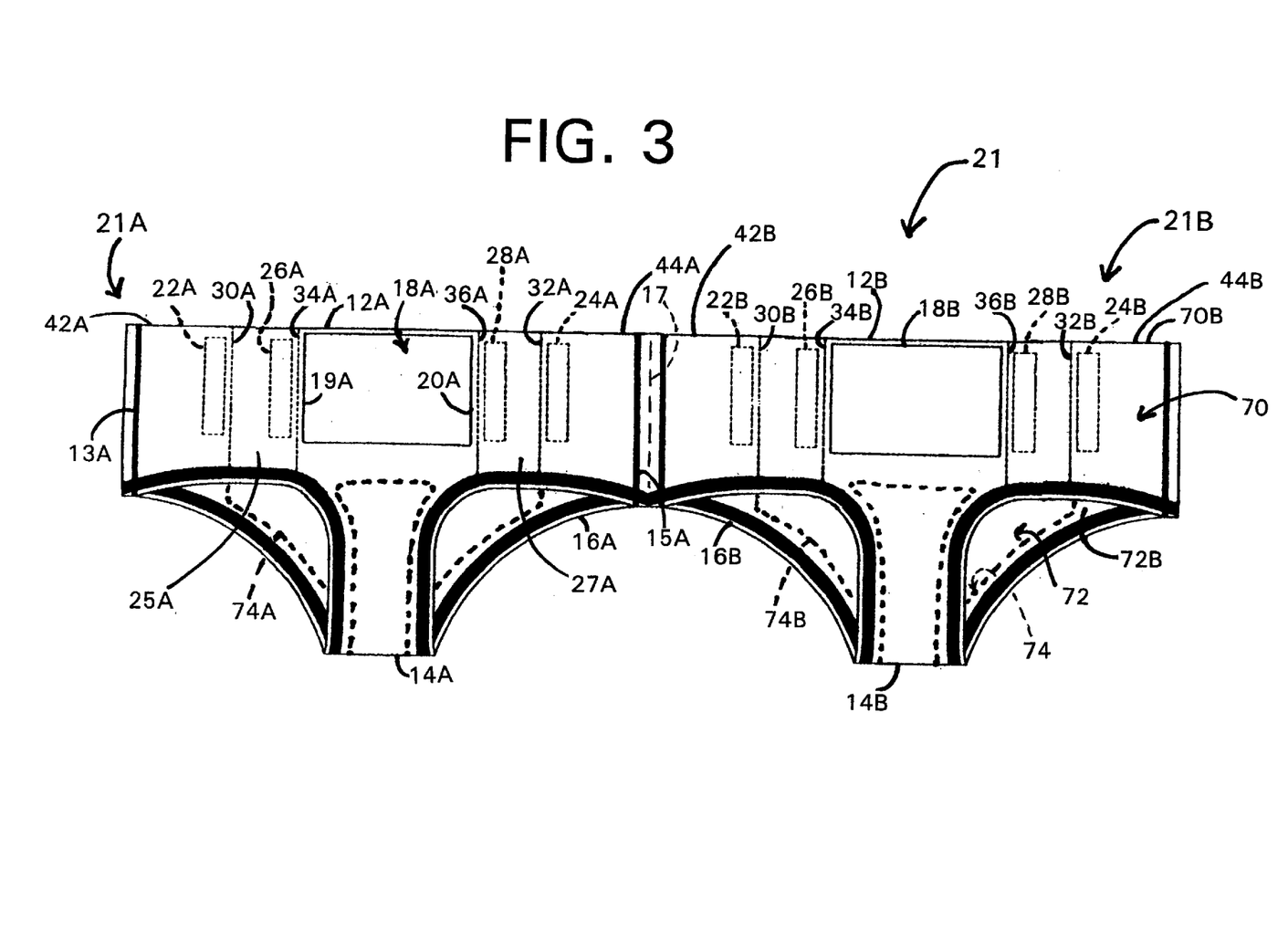
FIG. 3 illustrates, as another representative embodiment of personal care articles which can be made employing methods of the invention, the illustrated first and second personal care articles demonstrating adaptable sizing.

Referring to FIG. 3, as in FIGS. 1A and 1B, first and second ones of the personal care articles are illustrated employing "A" and "B" suffixes to represent elements of the respective first and second personal care articles. Thus, a personal care article of the invention generally comprises an outer liquid-impermeable cover 70, a liquid-permeable bodyside liner 72, and an absorbent core 74 disposed between outer cover 70 and bodyside liner 72.

Various woven and nonwoven fabrics can be used for bodyside liner 72. For example, bodyside liner 72 can be e.g. a meltblown or spunbonded or other non-woven web of polymeric material selected from the group consisting of polyolefins including polyethylenes and polypropylenes, polyesters, and polyamides, and mixtures, copolymers, and blends of such polymeric fibers. Bodyside liner 72 may also comprise a carded and/or bonded web composed of natural and/or synthetic fibers. The bodyside liner can be composed of a substantially hydrophobic material wherein the hydrophobic material is treated with a surfactant or otherwise processed to impart a desired level of wetability and hydrophilicity.

Bodyside liner 72 can comprise nonwoven, spunbonded, polypropylene fabric fabricated with 2.8–3.2 denier fibers, formed into a web having a basis weight of e.g. about 22 grams per square meter and a density of e.g. about 0.06 grams per cubic centimeter. The fabric is preferably surface treated with e.g. about 0.3 weight percent of a surfactant. Bodyside liner 72 typically comprises a fibrous web defining a multiplicity of small e.g. microporous openings randomly spaced between the fibers and according to location and orientation of the fibers, extending from a major surface of the web into the interior of the web. Such small openings typically extend through the entirety of the thickness of the web.

Addressing structure, bodyside liner 72 can be fabricated using material selected from the group consisting of porous foams, reticulated foams, apertured polymeric films, polymeric fibers, and natural fibers. Bodyside liner 72 can comprise a multiplicity of components or layers which correspond to any of the materials disclosed herein, as well as others known in the art.

It is generally preferred that outer cover 70 of the absorbent article be formed from a material which is substantially impermeable to liquids. A typical outer cover 70 can be manufactured from a thin plastic film or other flexible liquid-impermeable material. For example, outer cover 70 can be formed from a film of polymeric material selected from the group consisting of polyolefins including polyethylenes and polypropylenes, polyesters, and polyamides, and mixtures, copolymers, and blends of such polymeric materials, having thicknesses, for example, of from about 0.012 millimeter to about 0.13 millimeter.

In embodiments where outer cover 70 should have a more cloth-like feel, the outer cover can comprise a polyethylene film having a nonwoven web, such as a spunbonded web of polyolefin fibers, bonded to a surface thereof. For example, a polyethylene film having a thickness of about 0.015 millimeter can have thermally or otherwise bonded thereto a spunbonded web of polyolefin fibers having fiber thicknesses of from about 1.5 to about 2.5 denier per filament, which spunbonded web has a basis weight of e.g. about 24 grams per square meter.

Further, outer cover 70 can be formed of a woven or nonwoven fibrous web which has been totally or partially constructed or treated to impart a desired level of liquid impermeability to selected regions which are e.g. adjacent or proximate absorbent core 74.

Still further, outer cover 70 can optionally be composed of a micro-porous material which permits vapors to escape from absorbent core 74 and through outer cover 70 while preventing liquid exudates from passing through the outer cover.

One or both of outer cover 70 and bodyside liner 72 can comprise a fibrous web defining a multiplicity of randomly-spaced small openings extending from a major surface of the web into the interior of the web. Polymeric material such as the recited polyolefins including polyethylenes and polypropylenes, polyesters, and polyamides, and mixtures, copolymers, and blends of such polymeric materials can be used in either film form or in non-woven fiber form, for one or both of bodyside liner 72 and outer cover 70. As to bodyside liner 72, films are apertured films. As to outer cover 70, fibrous webs are impermeable to e.g. aqueous liquid.

Included in the definition of polymeric material above are all routine, common, normal additives known to those skilled in the art of polymeric materials such as processing aids, chemical stabilizers, compatibilizers e.g. where more than one polymer is used, fillers, and the like.

Absorbent core 74 suitably comprises hydrophilic fibers, such as a web or matt or loose collection of cellulosic fluff, in combination with a high-absorbency material commonly known as superabsorbent material. Absorbent core 74 preferably comprises a mixture of superabsorbent hydrogelforming particles and wood pulp fluff. In place of the wood pulp fluff, one can use synthetic, polymeric, meltblown fibers or a combination of meltblown fibers and natural fibers. The superabsorbent material can be substantially homogeneously mixed with the hydrophilic fibers or can be otherwise combined into absorbent core 74.

Alternatively, absorbent core 74 can comprise a laminate of fibrous webs and superabsorbent material or other suitable means of maintaining a superabsorbent material in a localized area. Absorbent core 74 can additionally comprise an un-creped through air dried paper web material known as UCTAD.

Absorbent core 74 can have any of a number of shapes. For example and without limitation, absorbent core 74 can be rectangular, I-shaped or T-shaped. In such products as e.g. refastenable absorbent articles, pants, and the like, absorbent core 74 is preferably narrower in the crotch portion than in the rear portion or the front portion, especially where the crotch portion of the absorbent article is narrower than the rear portion or the front portion.

The high-absorbency material in absorbent core 74 can be selected from natural, synthetic and modified natural polymers and materials. The high absorbency material can be inorganic material, such as silica gels, or organic compounds, such as cross-linked polymers. The high absorbency material refers to any structure or composition, along with associated process, which renders normally water-soluble material substantially water insoluble but swellable, whereby absorbent properties are available but the swelled material is substantially immobile after absorbing water-based liquid. Such superabsorbent material can be fabricated by creating e.g. physical entanglement, crystalline domains, covalent bonds, ionic complexes and associations, hydrophilic associations such as hydrogen bonding, and hydrophobic associations, or Van der Waals forces. Two such superabsorbents are DRYTECH® 2035 M and FAVOR® SXM 880. DRYTECH® available from the Dow Chemical Company, Midland, Mich. FAVOR® is available from Stockhausen, Inc., Greensboro, N.C.

Referring to personal care articles 10 of FIG. 1A and personal care articles 11 of FIG. 1B, each personal care article comprises a front portion 12, a rear portion 16, and a crotch portion 14 located between front portion 12 and rear portion 16. First side seam 13 and second side seam 15 of each respective personal care article adhere front portion 12 to rear portion 16 of each respective personal care article at the side seam location. A central transverse axis 40 traverses a central portion of each personal care article thereby to reflect two mirror image side-by-side halves of each personal care article.

A cut zone 23 is located between each pair of side seams 13, 15 associated with adjacent ones of the personal care articles on the manufacturing line. When fabrication of a given personal care article workpiece, in the web of personal care article workplaces being fabricated, has been completed in web form, the respective personal care article workpiece is separated from the web by severing the workpiece in cut zone 23, at a cut line represented by dashed line 17, thereby to create the stand-alone resultant personal care article, ready for e.g. packaging or other suitable treatment.

Fastener-receptive area 18, comprising a first side edge 19 and a second side edge 20, is disposed at a central region of front portion 12 of the outer cover of the personal care article. While fastener-receptive area 18 is displayed as being a one-component, generally rectangular-shaped piece of material, the fastener-receptive area can comprise a variety of shapes and sizes, and any desired number of separate components. Further, in some embodiments, some or all of the outer cover can comprise suitable landing zone material such that the landing zone properties are integral with the outer cover.

Therefore, a fastener-receptive area may or may not have distinct physical edges, depending on whether the fastening properties desired to be performed thereby (i) are provided by distinct separate e.g. landing zone component(s) or (ii) are integral with a surface of front portion 12.

Referring to personal care article 10A, first fastener 22A is disposed between first side edge 19A of fastener-receptive area 18A and first side seam 13A, and similarly, second fastener 24A is disposed between second side edge 20A of fastener-receptive area 18A and second side seam 15A. Between first side edge 19A of the fastener-receptive area and first fastener 22A is located a first line of weakness 30A. Similarly, a second line of weakness 32A is disposed between second side edge 20A of the landing zone and second fastener 24A.

Fasteners 22A, 24A as illustrated herein define attachment structures which, e.g. in combination with fastener-receptive area 18A, or the like, can be repeatedly fastened, released, adjusted and then refastened. Acceptable embodiments of fasteners can include, for example and without limitation, adhesives, cohesives, mechanical fasteners such as buttons and corresponding buttonholes, snaps and the like, as well as other fasteners known to those skilled in the art which can be repeatedly fastened and released. Hook and loop fasteners are preferred because of their associated versatility and consumer acceptance.

Fastener-receptive area 18A can be constructed from a material that preferably has e.g. loop properties or hook material properties. In the alternative, any material which can form a cooperative relationship with desired fastener materials, such as those suggested above, to provide repeatable fastening and releasing properties, is suitable for use as, or in place of, fastener-receptive area 18A.

Still referring to personal care article 10A, the area of front portion 12A which is disposed between e.g. first line of weakness 30A and second line of weakness 32A defines a central section 46A of front portion 12A of the personal care article. Such line of weakness can comprise, for example, a line of breakable perforations or cuts. Lines of weakness are designed and constructed to be readily broken, but only if and when desired by a user or manufacturer. If desired, ones of the lines of weakness can be broken before the personal care article is placed around the torso of the wearer, in order to improve body fit by changing the size of the personal care article as further described hereafter.

Again referring to personal care article 10A, a first lateral section 42A of front portion 12A is disposed between first line of weakness 30A and first side seam 13A. A second lateral section 44A of front portion 12A is disposed between second line of weakness 32A and second side seam 15A. First and second lateral sections, 42A and 44A respectively, can be disassociated from central section 46A at respective lines of weakness 30A and 32A. Fasteners 22A, 24A function to enable the first and second lateral sections to be re-fastened onto fastener-receptive area 18A of central section 46A and subsequently released, multiple times. Thus, the wearer or an assistant or caregiver can easily open and optionally remove the personal care article from the body of the wearer, and then refasten the personal care article on the wearer again, as desired.

The refastenable structure also enables the user to release, adjust, and subsequently re-fasten the personal care article onto the body of the wearer. For example, if the personal care article is too loose upon using the article as a pull-on, first and/or second lateral sections, 42A and 44A respectively, can be disassociated from central section 46A at respective lines of weakness 30A and 32A, whereupon fasteners 22A, 24A can be refastened to fastener-receptive area 18A at central section 46A. By moving fasteners 22A, 24A onto landing zone 18A, the user inherently reduces the size of the waist portion of the personal care article and thus obtains a tighter fit of the personal care article about the body of the wearer. Herein, "waist portion" shall mean that portion of the respective personal care article which is disposed upwardly of first and second leg openings 31A, 33A, respectively (generically, leg openings 31, 33).

Figure 2:
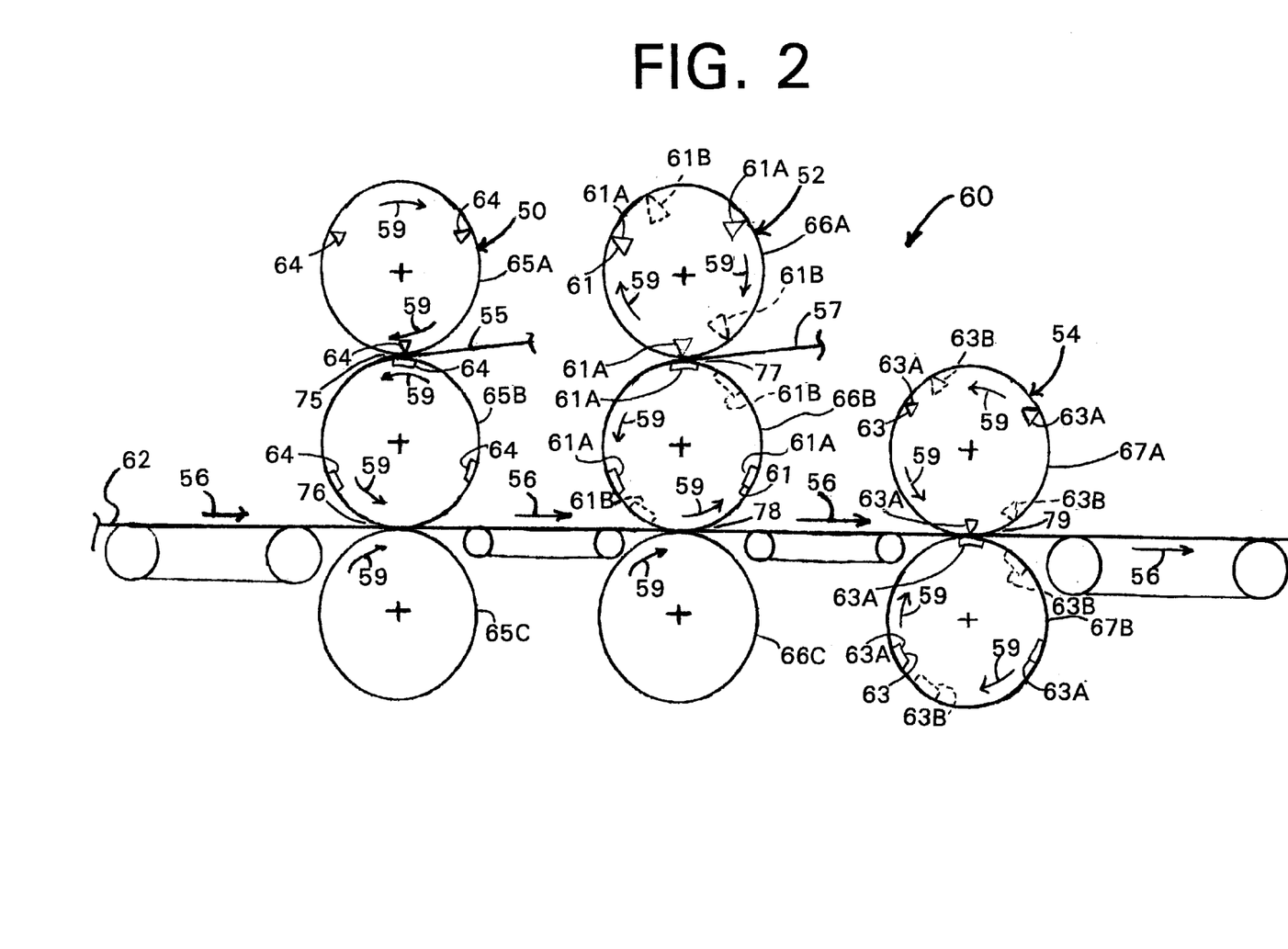
FIG. 2 shows a side elevation view of representative elements of a manufacturing line such as can be used in employing methods of the invention.

FIG. 2 illustrates a manufacturing line 60 such as can be used in processes employing methods of the invention. Web 62, being a personal care article precursor, is drawn or fed through manufacturing line 60 in the direction of manufacture indicated by arrow 56. Fastener-receptive area material 55 is applied to web 62 at landing zone feed apparatus 50. Fastener material 57 comprising at least first and second fasteners, e.g. 22A and 24A of FIG. 1A, are applied to web 62 by fastener feed apparatus 52. Web 62 is also affected by cutter apparatus 54, thus establishing first and second lines of weakness, e.g. 30A, 32A, in the personal care article precursor.

Referring to FIG. 2, landing zone feed apparatus 50 is disposed along manufacturing line 60 and comprises first, second, and third function rolls, 65A, 65B, and 65C respectively. Severing components 64 are disposed peripherally along first and second function rolls, 65A, 65B, thereby to sever landing zone material 55 as such material passes through nip 75, thus creating individual pieces of the landing zone material. The individual pieces of landing zone material are transported around second function roll 65B in direction of rotation 59, and such individual pieces of material are positioned and affixed to web 62 at desired locations as such pieces of landing zone material pass through nip 76, thus to produce personal care article precursors having landing zone areas.

Similarly, fastener feed apparatus 52 is also disposed along manufacturing line 60 and comprises fourth, fifth, and sixth function rolls, 66A, 66B, and 66C respectively. Sectioning components 61 are disposed at first positions 61A on fourth and fifth function rolls, 66A, 66B, thereby to effect cuts in fastener material 57 as such material passes through nip 77, thus creating individual segments of the fastener material. The individual segments of fastener material are transported around fifth function roll 66B in direction of rotation 59. As the segments of fastener material pass through nip 78, such individual segments of fastener material are positioned on and affixed to web 62 at first desired locations thus to produce personal care article precursors of a first size.

Cutter apparatus 54 is also disposed along manufacturing line 60 and comprises seventh and eighth function rolls, 67A, 67B, respectively. Cutter components 63 are disposed at first positions 63A on seventh and eighth function rolls, 67A, 67B, thereby to effect cuts/perforations in a cross-machine direction in at least portions of web 62 as web 62 passes through nip 79, wherein the cuts/perforations in the personal care article precursors of web 62 are homologous to lines of weakness, e.g. 30A, of personal care article workpieces, e.g. 10A, 10B, of a first size illustrated in FIG. 1A.

Preferably, to change sizing of the personal care articles produced using manufacturing line 60, sectioning components 61 of fastener feed apparatus 52 can each be relocated from respective first positions, e.g. 61A, to respective third positions, e.g. 61B, on fourth and fifth function rolls 66A, 66B of fastener feed apparatus 52, and similarly, cutter components 63 of cutter apparatus 54 can each be relocated from respective second positions, e.g. 63A, to respective fourth positions, e.g. 63B, on seventh and eighth function rolls 67A, 67B of cutter apparatus 54.

At FIG. 2, the illustration of positioning of sectioning components 61 at first positions 61A and third positions 61B is merely meant to be representative of a method of changing components in and out of third and fourth function rolls 66A, 66B to affect the spacing and placement of respective individual segments of fastener material on web 62 as web 62 proceeds in direction of manufacture 56. The illustration of sectioning components 61 at first positions 61A and third positions 61B is not to be construed as a scaled model reflecting a specific amount of change in spacing between positions 61A and 61B, nor is it to be construed to reflect scaled sizing of each of the respective components. The spacing and sizing of sectioning components. e.g. 61, on a function roll, e.g. 66A, is dependent upon, among other factors, the desired size and shape of each respective fastener, e.g. 22A of FIG. 1A, the diameter of the function roll being used, and/or the speed at which web 62 travel along direction of manufacture, e.g. 56, i.e. the rate of production of manufacturing line 60.

Additionally, the illustration of positioning of cutter components 63 at second positions 63A and fourth positions 63B is also merely meant to be representative of a method of changing components in and out of seventh and eighth function rolls 67A, 67B to affect the spacing and placement of respective cuts/perforations in web 62 as web 62 proceeds in direction of manufacture 56. The illustration of cutter components 63 at second positions 63A and fourth positions 63B is not to be construed as a scaled model reflecting a specific amount of change in spacing between positions 63A and 63B. The spacing of cutter components on a function roll, e.g. 67A, is dependent upon, among other factors, the desired width, length and pattern of each respective line of weakness, e.g. 30A of FIG. 1A, the diameter of the function roll being used, and/or the rate of production of manufacturing line 60.

Typically the timing of application of fasteners and creation of lines of weakness is maintained after such component relocations to thereby apply fasteners and implement lines of weakness at respective third and fourth desired locations on ones of respective personal care article workpieces, creating workpieces having second different waist sizes, e.g. 11A of FIG. 1B, but the same leading edge-to-leading edge repeat length as workpieces of the first size, e.g. 10A of FIG. 1A.

As an alternative, fastener feed apparatus 52 and, preferably, cutter apparatus 54 can each be relocated to respective fifth and sixth positions (not shown) in a machine direction along manufacturing line 60, typically while maintaining timing of application of fasteners and creation of lines of weakness, to thereby apply fasteners and implement lines of weakness at third and fourth desired locations on ones of respective personal care article workpieces, thus creating workpieces having second different waist sizes but the same leading edge-to-leading edge repeat length as workpieces of the first size.

"Machine direction", as applied herein, shall be understood to be synonymous to "with-machine direction".

It is also contemplated that size changes in personal care article workpieces can be accomplished by program changes to e.g. a programmable logic computer (not shown) which controls some or all of manufacturing line 60. Such programmable logic computer is can be communicatively connected to fastener feed apparatus 52 and/or cutter apparatus 54 thereby to effect desired timing and/or other programming changes to thereby effect size changes, or physical adjustments along the manufacturing line, to manufacturing line components, such as, but not limited to, a feed roll servo motor, landing zone feed apparatus, and mechanical phasing. Relocation of positioning of lines of weakness is made by e.g. repositioning the existing cutter apparatus, such as an application module knife, to new roll locations and/or adjusting mechanical phasing.

Repositioning of a respective fastener can be accomplished by, and includes, shrinking or expanding the size of the respective fastener element, e.g. 22A. Similarly, a side edge of a respective landing zone. e.g. 18A, can be laterally moved, either inward or outward, with relationship to the side seam disposed on the same side of the transverse axis, thus resulting in enabling a greater or lesser size capability of the respective personal care article workpiece. In some embodiments, the landing zone comprises two separate landing zone portions, each one positioned to receive one of the respective fasteners, e.g. 22A or 24A. While the implementation of two separate landing zone portions results in an additional piece of material to place, potentially less landing zone material can be used, resulting in reduced material cost.

Articles and methods of the invention accomplish waist circumference size changes between a relatively smaller personal care article and relatively larger personal care article by changing waist circumference. Waist circumference can be changed as follows. First, the user can break the lines of weakness 30A, 32A (e.g. FIG. 1A) and move the fasteners, e.g. 22A, 24A, onto the landing zone. Second, the manufacturer can change the location at which fasteners 22A, 24A are placed on the workpiece during assembly, as seen in a comparison of locations of the fasteners, e.g. 22A, 24A, in FIGS. 1A and 1B, and thus change waist size. Such change in location of placement is done by relocating fastener material and optionally lines of weakness in the machine direction in opposite directions away from the fastener-receptive area. The fastener-receptive area is disposed between the lines of weakness and between the respective fastener materials. As a result of changing location of placement of the fastener material during article manufacture, a larger effective distance of travel is created between each respective portion of fastener material, e.g. 22A, 24A, and fastener-receptive area, e.g. 18A, to which the fastener material is to be attached, thus providing for a greater degree of waist circumference change when the user breaks the line of weakness and moves the fastener material onto the fastener-receptive area.

In some embodiments, the method comprises, with respect to each workpiece, defining in the web or workpiece a length of material defined in a machine direction wherein activity of such length of material, in combination with other elements of the web or workpiece, determines the size of the article being produced, whereby the length of material can be activated to thereby produce relatively larger articles, or inactivated to produce relatively smaller articles. The method also comprises changing activity of the lengths of material so defined, thereby to affect size change in the respective articles being produced while maintaining the so-defined lengths of material in the web at least until the respective workpieces are separated from the web. In such embodiments, material is "activated" when such material is effectively used to affect the sizing of the article. Extra and/or waste material, as well as portions of the respective article extraneous to sizing of the article, defines "inactivated" material. Material portions of a respective article or article workpiece may be activated or inactivated by one or both the manufacturer and the wearer.

In preferred embodiments, the method includes such workpieces of FIGS. 1A and/or 1B, including the defined length of material, having a common dimension, leading edge to leading edge in the machine direction of such manufacturing process both with inclusion of the length of material and with exclusion of the length of material. Herein the term "leading edge to leading edge" defines the distance between respective side seams, e.g. 15A, 15B, or 13A, 13B, of adjacent absorbent article workpieces, e.g. 10A, 10B or 11A, 11B, in the machine direction of such manufacturing process.

Referring to absorbent article 10A of FIG. 1A, and article 11A of FIG. 1B as examples, location for placement of first fastener 22A and second fastener 24A are moved from the respective positions shown in FIG. 1A, outwardly on one or both lateral sections 42A and 42B to the respective positions shown in FIG. 1B while retaining the positionings of lines of weakness 30A and 32A relative to the positionings of fasteners 22A, 24A, to effect the change in the size of the wearer which the personal care article so manufactured will fit. Such change in the manufactured size can be implemented simply by changing timing of placement of fasteners e.g. 22A, 24A on lateral sections 42A, 44A. In the alternative, such change can be implemented by changing location of fastener apparatus as suggested by 52A and 52B in FIG. 2. As desired, the size change can be implemented by a combination of timing changes and location changes related to the fastener feed apparatus.

Given the changed fastener placement shown in FIG. 1B, and the increased distance which the fastener must traverse to reach its fastening location on landing zone 18A, the material between line of weakness 30A and landing zone 18A is effectively "inactivated" as far as determining size of the personal care article. By comparison, the same machine direction length of material forms part of the waist area or front portion of the personal care article in FIG. 1A, whereby such length of material is "activated" in the embodiments of FIG. 1A. Thus activation and inactivation are defined in terms of whether the respective length of material can be removed without affecting the size of the personal care article when used in the diaper-like article mode, with the fasteners fastened to the landing zone.

Referring to FIG. 1B, wherein fasteners 22A, 24A have been placed outwardly of the positions illustrated in FIG. 1A, such personal care articles are the same size as the personal care articles of FIG. 1A, as pull-ons or pants. When article 10A of FIG. 1A is used as a diaper-like article, by tearing lines of weakness 30A, 32A and repositioning the fasteners on landing zone 18A, fasteners 22A, 24A can be moved a short distance to the edge of the landing zone, or as far as axis 40A. By contrast, when article 11A of FIG. 1B is used as a diaper-like article, the smallest distances the fasteners can be moved to engage landing zone 18A is significantly greater than the smallest distance such fasteners can move on article 10A. Correspondingly, the greatest distances the fasteners of article 11A can be moved, e.g. to axis 40A is also greater than the greatest distance such fasteners can move on article 10A.

The net effect of the changed position of fasteners 22A, 24A in FIG. 1B is that the length of material 25 between e.g. line of weakness 30A and landing zone 18A can be removed without changing the size of article 11A when the article is used as a diaper-like article.

As suggested by FIG. 1B, lines of weakness e.g. 30A, 32A can be moved (relative to FIG. 1A) a distance corresponding to the changed positions of the respective fasteners 22A, 24A, as illustrated. In such case, length of material 25 is retained as part of the front portion of article 11A when the article is used as a diaper-like article, and is disposed e.g. against the wearer's skin when article 11A is being worn.

In the alternative, lines of weakness 30A, 32A can be left in the position of FIG. 1A, adjacent landing zone 18A, whereupon length of material 25 is retained with the respective fastener, and is disposed outside, and overlies, the landing zone. Thus the location of the line of weakness determines whether length of material 25A resides on the central front section or on the lateral section. Indeed, line of weakness e.g. 30A can, in principle, be positioned at any location between the locations shown in FIGS. 1A and 1B. If a respective line of weakness is disposed inwardly/centrally toward the fastener-receptive area, length of material 25 remains attached to the respective lateral section of the personal care article workpiece as part of the exterior surface of the article. Conversely, if the same line of weakness is disposed outwardly of the fastener-receptive area toward the respective fastener as in FIG. 1B, length of material 25 becomes part of the central front section, on the interior of the personal care article.

Since the fastener material locations and, optionally, locations of the lines of weakness are the only portions of personal care article of the invention which change with manufacturing size changes, no on-line waste is generated in the process. Length of material 25 which results from a such size adjustment remains with each individual personal care article.

FIG. 3 illustrates a further embodiment of the invention showing a first refastenable pant-type personal care article 21A and a second refastenable pant-type personal care article 21B, both reflecting further size adjustment capabilities. Respective first and second personal care articles are separated by prospective cut line 17 as in the embodiments of FIGS. 1A and 1B.

The personal care articles shown in FIG. 3 comprise front portions 12A, 12B, rear portions 16A, 16B, and crotch portions 14A, 14B located between front portions 12A, 12B and rear portions 16A, 16B. First side seams 13A, 13B and second side seams 15A, 15B of the respective personal care articles adhere front portions 12A, 12B to rear portions 16A, 16B of the respective personal care articles.

Fastener-receptive areas 18A, 18B, comprising first side edges 19A, 19B and second side edges 20A, 20B, are disposed at front portions 12A, 12B of the outer covers of the personal care articles.

Referring to personal care article 21A, first fastener 22A is disposed between first side edge 19A of fastener-receptive area 18A and first side seam 13A, and similarly, second fastener 24A is disposed between second side edge 20A of fastener-receptive area 18A and second side seam 15A. A third fastener 26A is disposed between first fastener 22A and first side edge 19A of fastener-receptive area 18A, and similarly, a fourth fastener 28A is disposed between second fastener 24A and second side edge 20A of fastener-receptive area 18A.

Between third fastener 26A and first fastener 22A is located a first line of weakness 30A. Similarly, a second line of weakness 32A is disposed between fourth fastener 28A and second fastener 24A. Additionally, a third line of weakness 34A is disposed between third fastener 26A and first side edge 19A of fastener-receptive area 18A, and a fourth line of weakness 36A is disposed between fourth fastener 28A and second side edge 20A of fastener-receptive area 18A.

The area of front portion 12A of personal care article 21A which is disposed between first line of weakness 30A and third line of weakness 34A defines a first sizing length of material 25A of the absorbent article. A second sizing length of material 27A is defined by the area of front portion 12A of the personal care article which is disposed between second line of weakness 32A and fourth line of weakness 36A.

In article 21A of FIG. 3, first lateral section 42A is disposed between third line of weakness 34A and first side seam 13A; and second lateral section 44A is disposed between fourth line of weakness 36A and second side seam 15A. First and second lateral sections, 42A and 44A respectively, can be separated from the central section 46A at respective third and fourth lines of weakness 34A and 36A. Ones of the third and fourth fasteners 26A, 28A can then function to enable the first and second lateral sections to be re-fastened onto fastener-receptive area 18A of central section 46A and subsequently again released, multiple times; thus, the wearer or an assistant or caregiver can easily remove the personal care article from the body of the wearer, and then refasten the personal care article on the wearer again, as desired, employing only a modest change in waist size from the size of the article when employed as a pant.

If a tighter fit, namely a smaller size personal care article effect, is desired than can be accomplished by attaching the third and fourth fasteners to fastener-receptive area 18A, first and second fasteners 22A, 24A can be engaged with the landing zone, effecting a smaller waist size of the personal care article on the wearer. Lengths of material 25A, 27A, thereupon become extraneous to the structure of the personal care article and can, if desired, be disassociated and from first and second lateral sections 42, 44. For example, lengths of material 25A, 27A can be torn away from the personal care article at lines of weakness 30A, 34A and 32A, 36A, and discarded. The embodiment of FIG. 3 thus provides for a single personal care article which affords all sizes available in the combined illustrations of FIGS. 1A and 1B, along with the wide range of adjustability inherent in FIGS. 1A and 1B, thereby enabling different wearers of a wide variety of shapes and sizes to use the same personal care article structure without having to pre-select a particular size, or to stock multiple sizes of personal care articles in order to achieve good fit on a variety of wearers.

The refastenable structure also enables the user to release, adjust, and subsequently re-fasten the personal care article onto the body of the wearer. For example, if the personal care article is too loose upon using the article as a pull-on, first and/or second lateral sections, 42A and 44A respectively, can be disassociated from central section 46A at respective lines of weakness 30A and 32A, and then refastened to fastener-receptive area 18A at central section 46A to obtain a tighter fit of the personal care article about the body of the wearer.

Personal care articles of the invention can be used in at least two different ways. First, ones of personal care articles 10A of FIGS. 1A and 11A of FIG. 1B, as shipped to the customer, can be used as pant-like structures. In such format, first and second lateral sections 42A and 44A are, and remain, attached separately to central section 46A at lines of weakness 30A and 32A, respectively. The pant-like structure is slipped onto the wearer without disassociating first and second lateral sections 42A and 44A from central section 46A of the respective personal care article at lines of weakness 30A and 32A.

Accordingly, the legs are inserted through the waist opening, and through the leg openings. The pant is then pulled upwardly until the leg openings are snugly positioned at the groin. The wearer or care-giver can adjust the fitting of the pant-like structure to create a better relative positioning of the waist portion of the respective personal care article about the torso of the wearer, directed toward comfort of the wearer, thus to improve the fit. Further adjusting to obtain a tighter fit can be done by subsequent grasping and pulling on first and second lateral sections 42A and 44A, away from central section 46A along lines of weakness 30A and 32A, respectively, thereby to release first and second lateral sections 42A and 44A from central section 46A. First and second fasteners 22A and 24A, respectively, of first and second lateral sections 42A and 44A are then moved over fastener-receptive area 18A and fastened to fastener-receptive area 18A of central section 46A, so as to achieve a better relationship between adjusted size of the respective personal care article and size of the wearer. Release and refastening of fasteners 22A and 24A can occur multiple times (e.g. an indeterminate number of times) to enable proper fitting throughout the expected use life of the personal care article. Fasteners 22A and 24A of first and second lateral sections 42A and 44A, respectively, can be adjusted individually or in combination with each other to create a relatively tighter or relatively looser fit, though all such fits are tighter than the fit of the pant article shown in FIGS. 1A and 1B wherein neither of the lines of weakness 30A, 32A have been broken.

The second method of using ones of personal care articles 10A of FIGS. 1A and 11A of FIG. 1B is to use ones of such articles as a diaper-like article. Before putting the diaper-like article on the prospective wearer, first and second lateral sections 42A and 44A are separated from central section 46A of the personal care article at lines of weakness 22A and 24A, and front portion 12A is pulled away from back portion 16A. In the method of using such article as a diaper-like article, the separation of first and second lateral sections 42A and 44A from central section 46A can be performed before packaging by the manufacturer, or can be performed anytime prior to or during use by the wearer. After the lateral sections are separated from the central section, the personal care article is laid on a preferably horizontal surface with the bodyside liner facing upwardly. The lower portion of the torso of the wearer (e.g. infant or adult) is then laid or otherwise moved onto back portion 16A of the personal care article. Front portion 12A is then brought frontwardly between the legs of the wearer and onto the torso of the wearer. Lateral sections 42A and 44A are fastened, via first and second fasteners 22A and 24A, to fastener-receptive area 18A, completing the application of the personal care article onto the wearer. With possible exception of the separation of the lateral sections from the central section at the respective lines of weakness, those skilled in the art will recognize the instant above description as a known method of putting a diaper-like article on a wearer.

In the embodiment illustrated in FIG. 3, personal care article 21A, as shipped to the customer can be used as a pant-like structure, as well. First and second lateral sections 42A and 44A are, and remain, attached to central section 46A at lines of weakness 34A and 36A respectively. Such pant-like structure is slipped on by the wearer without releasing lateral sections 42A and 44A from central section 46A, in the manner described above.

The wearer can adjust the fitting of the pant-like structure to create a better relative positioning of the waist portion of the article about the torso of the wearer, directed toward comfort of the wearer, thus to improve the fit. Further, decrease in size can be obtained by disassociating first and second lateral sections 42A and 44A from central section 46A by fracturing lines of weakness 34A and 36A. First and second lateral sections 42A and 44A can then be fastened, via third and fourth fasteners 26A and 28A, respectively, to fastener-receptive area 18A of central section 46A so as to achieve an improved relationship between size of personal care article 21A and size of the wearer.

Additional decrease in size can be obtained by removing first length of material 25A from first lateral section 42A and removing second length of material 27A from second lateral section 44A by respectively fracturing lines of weakness 30A and 32A, as well as lines of weakness 34A and 36A. First and second lateral sections 42A and 44A can then be fastened, via first and second fasteners 22A and 24A respectively, to fastener-receptive area 18A of central section 46A so as to achieve the desired smaller size.

Release and refastening of first and second lateral sections 42A and 44A via respective fasteners can occur multiple times (e.g. an indeterminate number of times) to enable proper fitting throughout the expected use life of personal care article 21A. Respective fasteners of first and second lateral sections 42A and 44A can be adjusted individually or in combination with each other to create a relatively tighter or relatively looser fit.

In principle, the just-described smaller size associated with use of fasteners 22A, 24A can be achieved with breakage of any one of the lines of weakness between each of the respective fasteners and the landing zone. However, where only one line of weakness is broken, the length of material 25A or 27A between the respective pairs of lines of weakness remains attached to the personal care article during use, which attachment is less preferred by some wearers. Accordingly, tearing of both lines of weakness on a respective side of the landing zone, and removal of the respective length of material 25A, 27A, or both, is preferred.

In the embodiment of FIG. 3, personal care article 21A can be used as a diaper-like article, as well. In use as diaper-like article, lateral sections 42A and 44A are disassociated from central section 46A at lines of weakness 34A and 36A, and front portion 12A is pulled away from back portion 16A, prior to use. Personal care article 21A is then laid on a preferably horizontal surface with bodyside liner 72A facing upwardly. The lower portion of the torso of the wearer (e.g. infant or adult) is then laid on back portion 16A of personal care article 21A. Front portion 12A is brought frontwardly between the legs of the wearer and onto the torso of the wearer. Lateral sections 42A and 44A are fastened, via respective fasteners, to fastener-receptive area 18A of central section 46A, completing the application of personal care article 21A on the wearer. If personal care article 21A demonstrates too loose a fit on the wearer, first and/or second lengths of material 25A and 27A can be removed allowing for first and/or second fasteners 22A and 24A to be attached to fastener-receptive area 18A for tighter fit. Except for the disassociation of lateral sections 42A and 44A from central section 46A at lines of weakness 34A and 36A (optionally also at lines of weakness 30A and 32A), those skilled in the art will recognize the instant above description as a known method of putting a diaper-like article on a wearer.

Alternative methods of putting on a diaper-like article of either of the embodiments of FIG. 1A, 1B, or 3 will be obvious to those of ordinary skill in the art. Such alternative methods include, but are not limited to, e.g. putting the diaper-like article on a wearer when such wearer is in a position other than lying down, e.g. standing, and/or when such wearer's slacks/pants are not entirely removed, but rather, lowered to expose the lower trunk and groin region of the wearer.

Preferred embodiments of FIGS. 1A, 1B, and 3 are illustrated and/or described as having landing zone material affixed to or integral with the outer cover of the respective absorbent article. Being cooperatively associated with the preferred location of the landing zone area, respective fasteners are preferably affixed to the interior portion, e.g. bodyside liner, of the respective absorbent article. While the preferred locations of the fasteners and landing zone are disclosed above, other embodiments are contemplated wherein the landing zone material is affixed to or integral with the bodyside liner, and the fasteners are affixed to the outer cover of the absorbent article.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:

1. In a process for manufacturing pant-type refastenable personal care articles, a respective such personal care article having a front portion, a rear portion, and a crotch portion, a fastener-receptive area at the front portion for receiving fasteners thereon, first and second fasteners on opposing sides of the fastener-receptive area, and first and second lines of weakness on opposing sides of the fastener-receptive area and between the fastener-receptive area and the respective first and second fasteners, for tearing first and second lateral sections of the front portion from a central section of the front portion, whereby the first and second fasteners are disposed on the respective first and second lateral sections, a method of changing from manufacture of such pant-type refastenable articles of a first size to manufacture of such pant-type refastenable articles of a second different size, the method comprising, in the manufacturing process, changing spacing between the fastener-receptive area and at least one of the first and second fasteners while maintaining the first and second lines of weakness between the fastener-receptive area and the respective first and second fasteners.

2. A method as in claim 1, including changing spacing between the fastener-receptive area and both of the first and second fasteners while maintaining the first and second lines of weakness between the fastener-receptive area and the first and second fasteners.

3. A method as in claim 1, including changing location of the respective fastener on the front portion.

4. A method as in claim 3, including changing location of the respective line of weakness to maintain spacing between the line of weakness and the respective fastener.

5. A method as in claim 3, including changing locations of both the first and second fasteners on the front portion.

6. A method as in claim 5, including changing locations of the lines of weakness to maintain spacing between the lines of weakness and the respective fasteners.

7. A method as in claim 3, the fastener-receptive area having first and second side edges facing the respective first and second fasteners, the method including changing location of at least one of the side edges of the fastener-receptive area.

8. A method as in claim 7, including changing location of the respective line of weakness to maintain spacing between the line of weakness and the respective side edge.

9. A method as in claim 7, including changing location of both the first and second side edges of the landing zone.

10. A method as in claim 9, including changing locations of the lines of weakness to maintain spacing between the respective lines of weakness and the respective side edges.

11. In a process for manufacturing pant-type refastenable personal care articles, a respective such personal care article having a front portion, a rear portion, and a crotch portion, a landing zone at the front portion for receiving fasteners thereon, first and second fasteners on opposing sides of the landing zone, and first and second lines of weakness between the respective fasteners and a central longitudinal axis of the personal care article, the first and second lines of weakness defining first and second side edges of the landing zone, whereby the first and second fasteners are disposed on the respective first and second lateral sections, and a central section of the front portion between the lines of weakness defines the landing zone, a method of changing from manufacture of such pant-type refastenable articles of a first size to manufacture of such pant-type refastenable articles of a second different size, the method comprising, in the manufacturing process, changing location of at least one of the first and second fasteners toward or away from the central longitudinal axis while maintaining the respective first or second line of weakness between the respective fastener and the central longitudinal axis.

12. A method as in claim 11, including changing location of the respective line of weakness to maintain spacing between the line of weakness and the respective fastener.

13. A method as in claim 11, including changing locations of both the first and second fasteners on the front portion.

14. A method as in claim 13, including changing locations of both lines of weakness to maintain spacing between the lines of weakness and the respective fasteners.

15. A method of manufacturing personal care articles comprising:

(a) manufacturing an indefinite number of personal care articles of a first size, each such personal care article having a front portion, a rear portion, and a crotch portion, and first and second opposing side seams connecting the front and rear portion to each other and thereby defining the front portions and the rear portions of the respective personal care articles between the side seams on the respective personal care articles;

(b) reducing size of the personal care articles being manufactured by changing, in each respective personal care article, spacing between respective elements in the front portion of the personal care article and thereby creating excess material in the front portion between the first and second side seams of each respective personal care article and, (c) retaining the excess material in the personal care articles through completion of manufacture, and packaging.

16. A method as in claim 15, including removing the excess material in the personal care articles at some point during manufacture and packaging.

17. A method of manufacturing personal care articles comprising the steps of:

(a) manufacturing an indefinite number of personal care articles of a first size, each such personal care article having a front portion, a rear portion, and a crotch portion, and first and second opposing side seams connecting the front and rear portion to each other and thereby defining the front portions and the rear portions of the respective personal care articles between the side seams on the respective personal care articles;

(b) reducing size of the personal care articles being manufactured by changing, in each respective personal care article, spacing between respective elements in the front portion of the personal care article and thereby creating excess material in the front portion between the first and second side seams of each respective personal care article; and (c) manipulating respective excess material in each of the personal care articles at some point during manufacture or by the user wherein the excess material is repositioned and retained on the front portion, or folded over and retained on an interior of the respective personal care article, the interior formed when the excess material is folded over, the excess material being configured for subsequent repositioning, unfolding, retention and combinations thereof.

18. The method as in claim 17, further comprising the step of:

creating a line of weakness in the respective personal care article to define a central section of the front portion, the line of weakness configured to be readily broken.

19. The method as in claim 18, further comprising the step of:

disposing the line of weakness closer to a fastener-receptive area such that the excess material overlaps the front section or farther from the fastener-receptive area such that the excess material underlaps in the interior of the front section when manipulated.

20. The method as in claim 18, further comprising the step of:

breaking the line of weakness before placing the personal care article about a torso of a wearer.

* * * * *